United States Patent
Jacobs et al.

(10) Patent No.: US 8,313,713 B2
(45) Date of Patent: Nov. 20, 2012

(54) STABILIZING A CUVETTE DURING MEASUREMENT

(75) Inventors: Merrit N. Jacobs, Fairport, NY (US); Robert Anthony Burkovich, Pittsford, NY (US); David Lee Johnson, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 1053 days.

(21) Appl. No.: 10/870,107

(22) Filed: Jun. 17, 2004

(65) Prior Publication Data

US 2005/0281715 A1    Dec. 22, 2005

(51) Int. Cl.
*G01N 21/00* (2006.01)

(52) U.S. Cl. .......................................... 422/554; 422/65

(58) Field of Classification Search .................. 356/246; 422/63, 64, 554, 65; 436/47
See application file for complete search history.

(56) References Cited

U.S. PATENT DOCUMENTS

| | | | | |
|---|---|---|---|---|
| 3,428,174 | A | * | 2/1969 | Kulig ............................. 209/526 |
| RE30,391 | E | | 9/1980 | Liston |
| 4,366,118 | A | * | 12/1982 | Bunce et al. .................... 422/57 |
| 4,517,160 | A | | 5/1985 | Galle et al. |
| 4,595,562 | A | | 6/1986 | Liston et al. |
| 4,634,575 | A | * | 1/1987 | Kawakami et al. ............. 422/63 |
| 4,636,477 | A | | 1/1987 | Ronka et al. |
| 4,639,135 | A | | 1/1987 | Borer et al. |
| D290,170 | S | | 6/1987 | Kayhko |
| 4,690,900 | A | | 9/1987 | Kimmo et al. |
| 5,104,807 | A | * | 4/1992 | Mitsumaki et al. ............. 436/47 |
| 5,380,666 | A | | 1/1995 | Wuerschum |
| 5,774,209 | A | | 6/1998 | Shestock |
| 5,849,247 | A | | 12/1998 | Uzan et al. |
| 6,328,164 | B1 | | 12/2001 | Riekkinen et al. |
| 2003/0003591 | A1 | | 1/2003 | LaCourt et al. |
| 2003/0022380 | A1 | | 1/2003 | Jakubowicz et al. |
| 2003/0104634 | A1 | | 6/2003 | Jacobs et al. |
| 2005/0078307 | A1 | | 4/2005 | Freeman et al. |
| 2005/0185176 | A1 | | 8/2005 | Moran et al. |

FOREIGN PATENT DOCUMENTS

CA    2019511    9/1994

(Continued)

OTHER PUBLICATIONS

European Search Report, dated Sep. 7, 2005, for European Appln. No. EP 05253761.
Beebe, Kenneth R. et al., "An Introduction to Multivariate Calibration and Analysis", Analytical Chemistry, vol. 59, No. 17, Sep. 1, 1987, pp. 1007A-1017A.

(Continued)

*Primary Examiner* — Lore Jarrett
(74) *Attorney, Agent, or Firm* — Todd J. Burns

(57) ABSTRACT

A device and method solves the problems of improving precision, in particular in reducing movement of a cuvette, particularly lateral or side to side movement of a cuvette, during the measurement process. The device, which stabilizes a cuvette during a measurement read in an analyzer having a cuvette path of travel, includes: a fixed support located on a first side of the path of travel and abutting a side of the cuvette at a location that does not interfere with an optical window on the cuvette on which the measurement read takes place; and a movable support located on a second side of the path of travel and biased against a side of the cuvette at a location that does not interfere with the optical window on the cuvette on which the measurement read takes place, and which is opposite the side abutting the fixed support.

14 Claims, 6 Drawing Sheets

FOREIGN PATENT DOCUMENTS

| | | |
|---|---|---|
| DE | 4214161 | 11/1993 |
| EP | 0843171 | 5/1998 |
| JP | 58140459 A | 8/1983 |
| JP | 58146839 A | 9/1983 |
| JP | 60085521 A | 5/1985 |
| JP | 2003083995 A | 3/2003 |
| WO | WO 02/066096 A2 | 8/2002 |
| WO | WO 2004/027375 A3 | 12/2004 |

OTHER PUBLICATIONS

Hall, Jeffrey W. et al., "Near-Infrared Spectrophotometry: A New Dimension in Clinical Chemistry", Clinical Chemistry, vol. 38, No. 9, 1992, pp. 1623-1631.

Thomas, Edward V., "A Primer on Multivariate Calibration", Analytical Chemistry, vol. 66, No. 15, Aug. 1, 1994, pp. 795A-804A.

* cited by examiner

STABILIZING A CUVETTE DURING MEASUREMENT

BACKGROUND OF THE INVENTION

The present invention relates to measuring the presence or concentration of an analyte in a sample, particularly by spectrophotometry. In particular, the present invention relates to a device and method for stabilizing a cuvette while the cuvette is in the measurement station of an analyzer.

Spectrophotometer and photometer measurement systems have historically been designed so that the cuvette is motionless during the read or measurement process. See, e.g., U.S. Pat. No. 5,774,209. To increase system throughput, specialized spectrophotometers and photometers have been designed to take readings while the cuvette is moving. A related class of moving cuvette measurement systems stops the motion of the cuvette and immediately takes a reading. The shorter delays after cuvette motion stops, and the shorter read integration times result in faster system cycle time and generally translates into more tests processed per hour, i.e., higher throughput. Throughput of a system is an important measure that determines the value of an analyzer system to users and is of significant importance in marketing diagnostic analyzers. Known diagnostic analyzers having cuvettes include those described in U.S. Pat. Nos. 4,595,562; 5,774,209; 5,849,247; 4,517,160; 5,380,666 and Re. 30,391.

Some known analyzers, such as the Vitros® Fusion 5,1 analyzer developed by Ortho-Clinical Diagnostics, Inc. or Konelab™ 60 sold by Thermo Electron Corporation use a multi-cell cuvette as shown in FIG. 1, containing rows of separate test cells, such as a row of 6 or 12 separate test cells. The entire cuvette consisting of, e.g., 6 cells must be read very quickly, on the order of about 1.5 seconds to keep up throughput. The design is to read each of the cells after it has stopped. As described in copending patent application Ser. No. 10/784,505, filed Feb. 23, 2004, entitled "Determining An Analyte By Multiple Measurements Through A Cuvette", which is incorporated herein by reference in its entirety, the preferred measurement read process is to take multiple measurement readings (preferably 3) at each of the 6 cells in a cuvette during each read cycle. By taking three measurement reads per cell, the cuvette needs to start/stop 18 times for each row of 6 cells. The larger number of reads require a shorter integration time for each measurement read (20 ms instead of the standard 100 ms).

Tests with the cuvette being completely static showed that a reduction in measurement read integration time to 20 ms does not substantially degrade photometer precision. However, in some cases, such as large number of measurement reads in short period of time, there was substantial degradation in photometer precision. In fact, actual test data with the cuvette stopped immediately before the measurement read demonstrated that the shorter integration times were often 10 times to 100 times more imprecise. If there was any movement, it was believed in the art that the chopping system for the photometer would cancel out errors due to movement of the cuvette during the measurement read process. However, this was not the case.

The problem of cuvette imprecision was particularly noticeable in systems in which the cuvette is supported at one end by the cuvette handling system, such as by a hook or other devices, such that the cuvette is cantilevered. In those systems, test data showed a pattern where the last three cells in the cuvette (the ones furthest away from a conveyor system that captures the cuvette by cantilevering the cuvette at one end) were often significantly more imprecise. In addition, the data also showed that the first of the three measurement reads within a cell was often more precise than the other two.

None of the known art described above, adequately addresses resolving the problems described above, in particular, of improving precision of measurements in multi-cell cuvettes in the measurement station of an analyzer For the foregoing reasons, there is a need for a device and method to improve the precision of measurement reads in a multi-cell cuvette.

SUMMARY OF THE INVENTION

In order to determine the causes of the imprecision, the inventors conducted an extensive investigation, including using high speed video analysis during the measurement read process. As a result of the investigation, it was discovered that there was residual motion remaining in the cuvette when the measurement read takes place. That is, although the cuvette is not intentionally moving at the time of the measurement read, it was moving just before the measurement read such that there was residual motion in the cuvette driven by oscillations still occurring after the cuvette has stopped.

Cuvette motion is not a significant issue in conventional systems that have larger measurement read integration times (e.g., 100 ms) because of the large number of reads (e.g., 350 sample and 350 reference reads/100 ms) as opposed to smaller number of reads in systems that have shorter integration times (e.g., 70 sample and 70 reference reads/20 ms). That is, with larger integration times, the residual motion of the cuvette stops quickly enough such that a smaller number of actual reads are affected by motion and the effect of these reads is attenuated by the large number of reads with no motion. However, in the case of short integration times, many more of the reads are affected by motion, thus leading to the imprecision problem.

Prior to the present invention, it was widely believed that motion of the cuvette would not affect the measurement read due to chopping systems used in measurement stations of analyzers. That is, the chopping system would account for any motion and effectively cancel out variations in motion, because the sample read and reference read would be at the same angle. Changing the cuvette angle relative to the light source and detector will change the travel path of the light beam. If the angle is significant, the light will reflect off the side walls of the cuvette back into the reference and sample collection photodiode affecting the energy detected. As long as the angle is relatively consistent between the reference and sample collection, the error associated with the side wall reflection will cancel out. Testing of a static cuvette confirmed that when the cuvette's angle was changed relative to the light source and detector the was no significant change in the precision or the mean measured absorbance. These results were consistent with the understanding in the art that by doing a chopped measurement, variations in path length, etc. would be blanked out.

This was not the case in the present invention. While not wishing to be bound by any theory, the inventors believe that the ability of a chopping system to blank out or cancel out variations will only be correct as long as the motion of the cuvette is very slow compared to the chopping speed. Instead of slow cuvette motion, the inventors' findings showed that the frequency of a cuvette's motion is often times close to the frequency of the photometer sample/reference chopper system. As a result, it is believed that the cuvette angle changes within the shortened measurement read interval (e.g., 20 ms), leading to the condition where the cuvette is at a different angle between the reference and signal readings even though a chopping system is used.

The inventors' investigation also explained why in certain multi-cell embodiments, some cells, such as the last three cells of cantilevered cuvettes are more imprecise than others in the same cuvette. Specifically, the increased imprecision is due to increased motion. In the case of cantilevered cuvettes according to a preferred embodiment, such as those shown in FIG. 1, mounting the cuvettes on the conveyor system by cantilevering them (i.e., holding the cuvettes at one end) makes the cuvette more vulnerable to motion during the measurement process, particularly those cells farthest away from the attachment to the conveyor system.

Another related problem was the issue of imprecision in those embodiments using multiple measurement reads within a single cell, such as described in the copending '505 application. As used herein, "measurement read" should be distinguished from "read(s)" as used above. A measurement read will have numerous reads (both sample and reference reads) depending on the integration time. For example, in one embodiment, a measurement read having a 20 ms integration time would have 140 reads (70 sample and 70 reference). It would have been expected that, if there was any imprecision, the first measurement read within a cell would be the most imprecise, since it would the most vulnerable to motion. That is, the first measurement read in the cell would be after the cuvette had moved the length of at least one full cell, as opposed to later measurement reads, which occur after incremental moving within the same cell. Thus, the first measurement read having occurred after the greatest amount of movement would have been expected to be the least precise. The middle measurement read(s) occurring near the center of the cell would be expected to be the most precise because the belief, prior to the present invention, that imprecision was driven by internal reflection from the side-walls of the cuvette. However, exactly the opposite was true in that the first measurement read was the most precise of the multiple measurement reads within the cell. High speed video analysis, showed that the movement (in the direction P as shown in FIG. 2) before measurement read number one was a longer distance, which allowed for cuvette vibration to be stabilized before the first measurement read as opposed to the subsequent measurement readings, which were taken after only very short incremental displacement of the cuvette. Again, the present invention was found to address this source of imprecision by damping or eliminating lateral movement of the cuvette.

Thus, the present invention includes a device and method that solves the foregoing problems of improving precision, in particular in reducing movement of a cuvette, particularly lateral or side to side movement of a cuvette, during the measurement process.

One aspect of the invention is directed to a device for stabilizing a cuvette during a measurement read in an analyzer having a cuvette path of travel. The device includes: a fixed support located on a first side of the path of travel and abutting a side of the cuvette at a location that does not interfere with an optical window on the cuvette on which the measurement read takes place; and a movable support located on a second side of the path of travel and biased against a side of the cuvette at a location that does not interfere with the optical window on the cuvette on which the measurement read takes place, and which is opposite the side abutting the fixed support.

Another aspect of the invention provides a device for stabilizing a cuvette during a measurement read in an analyzer having a cuvette path of travel. The device includes: fixed support means for abutting a side of the cuvette at a location that does not interfere with an optical window on the cuvette on which the measurement read takes place; movable support means for biasing against a side of the cuvette at a location that does not interfere with the optical window on the cuvette on which the measurement read takes place, and which is opposite the side abutting the fixed support means; and biasing means for applying a biasing force against the movable support means in a direction toward the fixed support means.

Another aspect of the invention provides an analyzer for analyzing a sample. The analyzer includes: a cuvette supply; one or more cuvettes; a sample supply; a metering station for metering sample from the sample supply into the cuvette; an optical measurement station having a light source and detector for taking an optical measurement read of the sample, wherein the path of the light source and detector forms a measurement window; a cuvette conveyor for conveying cuvettes from the cuvette supply to the metering station and to the optical measurement station; and the device for stabilizing a cuvette described above, located in the optical measurement station, wherein the light source is located on the first or second side of the path of travel and the detector is located the other side of the path of travel.

Another aspect of the invention provides a method for stabilizing a multi-cell cuvette during measurement read for the presence or concentration of an analyte in a sample by spectrophotometry. The method includes: providing the device for stabilizing the cuvette as described above, located in an optical measurement station; transporting the cuvette into the optical measurement station between the fixed support and the movable support of the device for stabilizing; and biasing the movable support against the side of the cuvette, whereby the cuvette is sandwiched between the fixed and movable support to reduce lateral movement of the cuvette in the optical measurement station.

Another aspect of the invention provides a method for measuring the presence or concentration of an analyte in a sample. The method includes: providing a cuvette having a sample with an analyte to be measured; providing an optical measurement station having a light source and a detector for detecting emitted light for taking a spectrophotometric measurement read of the sample; providing the device for stabilizing the cuvette as described above, located in the optical measurement station; transporting the cuvette into the optical measurement station; stabilizing the cuvette with the device for stabilizing; taking at least one measurement read that includes: (i) directing at least one beam of light from the light source to the cuvette; (ii) passing the at least one beam through the cuvette and through the sample to be measured; and (iii) measuring at least one emitted light beam with the detector.

Yet another aspect of the invention provides a method for measuring the presence or concentration of an analyte in a sample by spectrophotometry. The method includes: providing a cuvette having a sample with an analyte to be measured; providing an optical measurement station having a light source and a detector for detecting emitted light for taking a spectrophotometric measurement read of the sample; providing the device for stabilizing the cuvette as claimed in claim 1, located in the optical measurement station; taking at least two measurement reads that include: (i) directing at least two beams of light from the light source to different locations on the cuvette; (ii) passing the at least two beams through the cuvette at their respective locations and through the sample to be measured; and (iii) measuring at least two respective emitted light beams with the detector; and comparing the at least two emitted light beams to determine if: all the emitted light beams should be disregarded; one or more of the emitted light beams should be disregarded; or the sample absorbances should be averaged.

According to another aspect of the invention, the method described above is implemented by a computer program interfacing with a computer. Another aspect of the invention provides an article of manufacture comprising a computer usable medium having computer readable program code configured to conduct the method described above.

Further objects, features and advantages of the present invention will be apparent to those skilled in the art from detailed consideration of the preferred embodiments that follow.

DETAILED DESCRIPTION OF PREFERRED EMBODIMENTS

Figure 1:
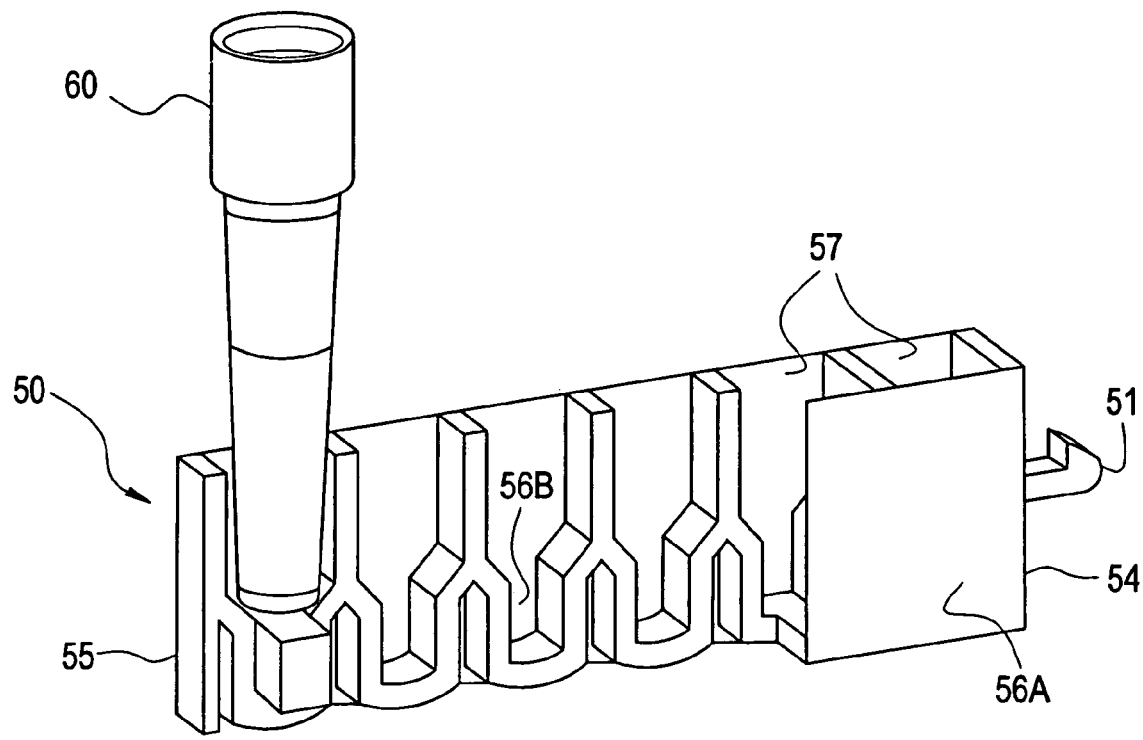
FIG. 1 is a partial cutaway schematic diagram showing a cantilevered cuvette usable with the present invention.

To assist in minimizing or even substantially eliminating the motion of the cuvettes, one aspect of the present invention includes a device for stabilizing a cuvette. The device is generally arranged in the path of cuvette travel in the measurement station of an analyzer. The analyzer can include any known instrument capable of taking a measurement of a previously unknown or unquantified analyte in a sample and through measurements and further processing, such as data processing either by hand or through the use of a computer or CPU, provide an indication of the presence of an analyte and/or the quantity of an analyte in the sample. In a preferred embodiment, the analyzer is a diagnostic analyzer, such as a clinical or immunodiagnostic analyzer and the sample is blood, serum or plasma. Other analyzers that would benefit from the present invention include analyzers such as chemistry analyzers used in a setting such as a chemistry laboratory or industrial setting.

Not shown herein nor described in any detail is the measurement station, preferably an optical measurement station since they are well known in the art. The optical measurement station includes a light source and detector for taking an optical measurement of the sample. In a preferred embodiment, the optical measurement station is a light tight enclosure into which the cuvette is inserted for a measurement. The path of light formed by the light source and detector forms a read or measurement window (shown as 52 in FIG. 3). The measurement station also includes a chopping system that splits a beam of light into a sample beam and reference beam. These systems are well known in the optical measurement art.

In a preferred embodiment a spectrophotometer is used in the optical measurement station. Any spectrophotometer is useful, provided it generates and detects via transmission, radiation emitted in the near infrared and adjacent visible light regions with sufficient spectra precision. As used herein, "near infrared and adjacent visible" means, radiation between about 400 and 2500 nm, and most preferably, between about 300 and 1100 nm. As used herein, "spectrophotometric" means a technique that captures the spectral response over a range of wavelengths and correlates a response for each wavelength in the range. As also used herein, "photometric" means an analysis of light radiation to correlate a response to only a particular wavelength. A "spectrophotometer" then is the apparatus that does spectrophotometric analysis. Unless indicated otherwise, "spectrophotomer" and "spectrophotometric" encompass "photometer" and "photometric," "fluorimetry," "reflectometry" and "chemiluminesence." No details are provided as to the mathematical analysis involved in correlating the amount of transmission of the near infrared and adjacent visible radiation through the sample, e.g., biological liquid, with the concentration of the target substance or analyte. The reason is that such is well-known, as is evident from Canadian Patent No. 2,019,511; the article in Clin. Chem., Volume 38,Pages 1623-1631 (1992); and the tutorial articles in Anal. Chem., Volume 59, Number 17, Pages 1007A-1017A (September 1987) and Anal. Chem., Volume 66, Number 15, Pages 795A-804A (August 1994).

A cuvette is provided for containing the sample. In a preferred embodiment, the cuvette is an open top cuvette adapted for receiving the tip (60, FIG. 1) of a pipette or proboscis which dispenses or aspirates sample and/or reagents into the cuvette, such as those described for example in U.S. patent application publication No. 2003/0003591 A1, Des. 290,170 and U.S. Pat. No. 4,639,135, all of which are incorporated by reference in their entireties and as shown in FIG. 1. Particularly preferred are cuvettes having a plurality of vertically disposed reaction chambers side-by-side in spaced relation, each of said reaction chambers 57 having an open top and being sized for retaining a volume of sample or reagent as described in the '591 published application. Each of the chambers are preferably arranged side-by-side and have at least one optically transparent window pair 56a, 56b to measure an optical property of the sample in the chamber, when the optically transparent window pair are aligned with the measurement window of the measurement device.

Figure 2:
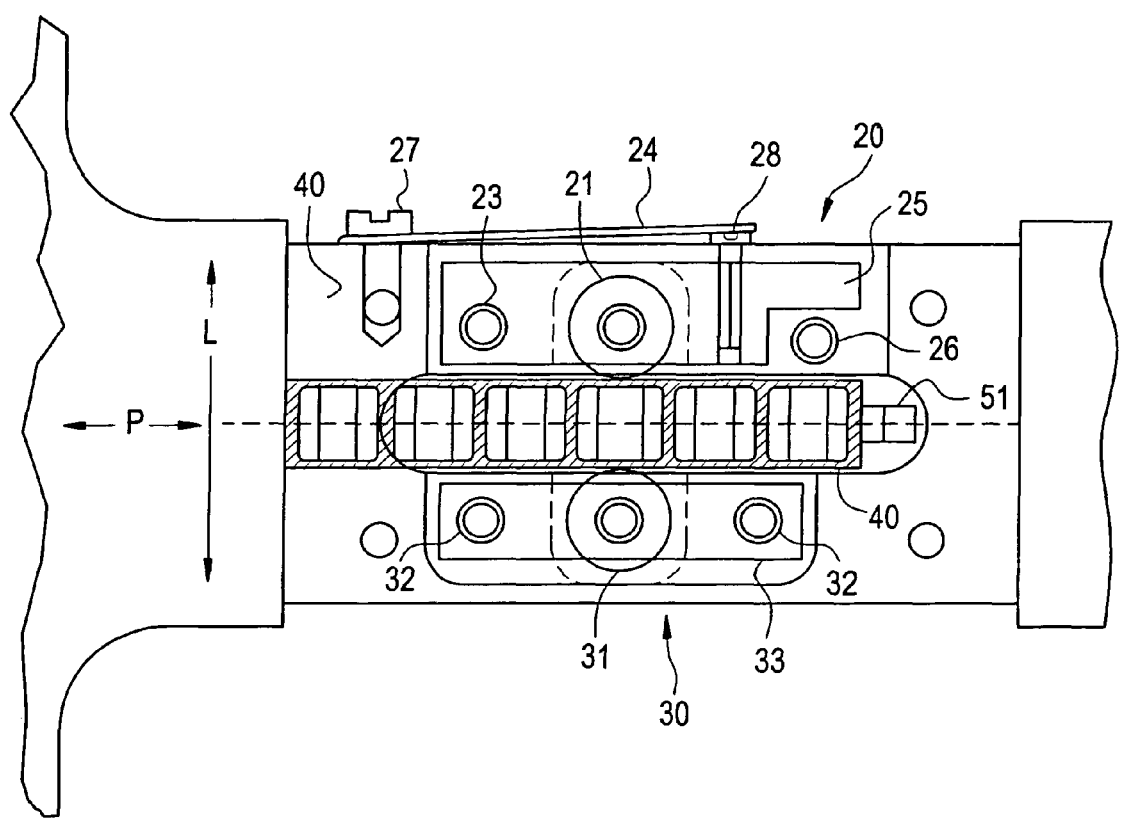
FIG. 2 is a top view schematic diagram of the stabilizing device according to the present invention and a cuvette in a measuring station of an analyzer.

Broadly, the device for stabilizing the cuvette includes a fixed support and a movable support. The fixed support or fixed support means is arranged on a first side of the path of travel of the cuvette. As described above, the path of travel is preferably in the measurement station of an analyzer. The fixed support is arranged to abut the cuvette as the cuvette passes by. The support abuts the cuvette in a such a fashion that the support does not interfere with the area on the cuvette (i.e., optically transparent window) where the measurement will take place. For example, the optically transparent window, i.e., read area on the cuvette may be in the center-bottom of the cuvette 56A, 56B and the support may abut the cuvette at the top as shown in FIG. 2. The fixed support can include any suitable structure for abutting against the cuvette as it passes along the path of travel. In addition to the preferred structure shown in FIGS. 2 and 3, other structures, such as a low friction static mechanism, e.g., a Teflon coated arm or rod can also be used. If a rod or arm is used, with or without the roller shown in the figures, the rod can be arranged either horizontally or perpendicularly. For example, a roller bearing or Teflon coated wiping structure could be supported at the proximate end of a vertically extending rod or arm with the distal end being immovably attached to the measurement station.

The movable support or movable support means is arranged on a second side of the path of travel of the cuvette opposite the fixed support. The movable support is biased against the side of the cuvette in a manner that does not interfere with the area of the cuvette where measurement takes place (i.e., the optically transparent window) in a manner analogous to the fixed support. The movable support can include any suitable structure for abutting and biasing against the cuvette as it passes along the path of travel. Preferably, the combination of the fixed and movable support only exerts a lateral force, i.e., a force perpendicular to the path of travel to the cuvette as it passes through the measurement station.

An important distinction between the fixed and movable support is that the movable support is capable of biasing or pressing against the side of the cuvette to provide the lateral force necessary for stability. The movable support preferably includes the structure described in the embodiment shown in FIGS. 2 and 3. However, other suitable structures can also be used. For example, like the fixed support, the movable support can include a low friction member, e.g., a Teflon coated arm or rod, arranged either horizontally or vertically. To bias against the cuvette, at least one portion of the movable member has to be capable of moving in a direction transverse to the motion of the cuvette along the path of travel. The member can have a distal end attached to the frame of the analyzer or measurement station, as in the embodiment shown in the figures, with the proximal end of the member unattached. Alternatively, the member can have the distal end movably attached with the proximal end which contacts and biases against the cuvette being free. For example, a roller bearing or Teflon coated wiping structure could be supported on the proximate end of a vertically extending rod or arm with the distal end being movably attached to the measurement station. When the distal end is moved in a direction toward the cuvette by a biasing device or means (described below), the roller bearing or wiping structure will be biased against the cuvette moving along the path of travel.

The movable support is laterally biased in the direction perpendicular to the path of travel of the cuvette by a biasing device or biasing means. The biasing device can include a spring (either a leaf spring described in connection with the FIGS. 2 and 3 below or a coil spring described in connection with the FIGS. 4 to 6 below) that will apply a variable force in accordance with Hook's law, or a device to apply a constant force such as a weight or a hydraulic or pneumatic press.

Both the movable and fixed support will preferably abut the cuvette at a location on the cuvette that is directly above or below the area of the cuvette, where the measurement read is taken.

Now description will be made in connection with the preferred embodiments shown in the figures. The inventors have found that the lateral (or side to side) motion control is most preferably achieved by a roller bearing induced side load at the optically transparent window of the cuvette because it most expediently addresses the following factors:

(a) the device for stabilizing preferably has little tangential force on the cuvette;

(b) in those embodiments which employ a cantilevered cuvette, the device for stabilizing does not cause the cuvette to become dislodged from the cuvette pick up arm;

(c) the center point of the biasing force is preferably lined up with the measurement window; and (d) the cuvette design needed to have a region where the device for stabilizing could make contact with it but be outside of the optically transparent window so that it does not scratch or change the optical characteristics of the window.

Figure 3:
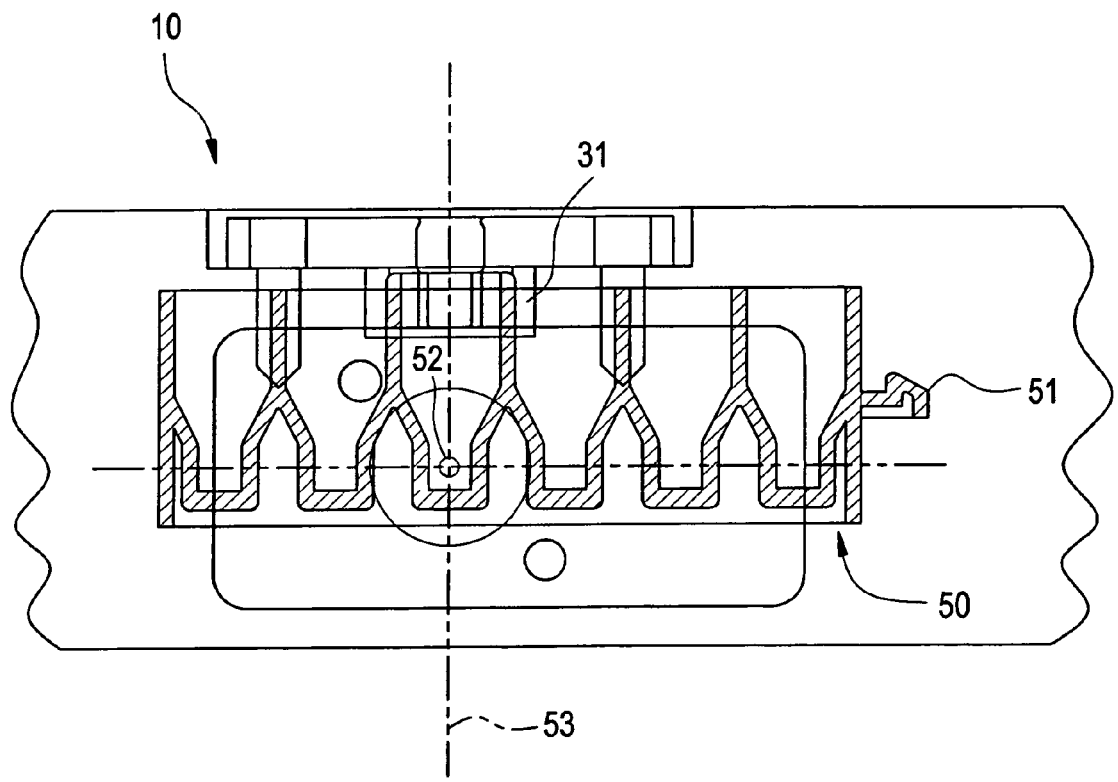
FIG. 3 is a schematic superimposed side view showing the different layers of the stabilizing device according to the present invention and a cuvette in a measuring station of an analyzer.

A preferred structure of the device 10 is shown in FIGS. 2 and 3. The movable support 20 and the fixed support 30 each include a roller bearing 21, 31, respectively, that are biased against the cuvette. As shown in FIG. 2, arm 33 supports roller bearing 31. As also shown in FIG. 2, the movable support includes an arm 22 pivotably attached to a fixed portion of the measurement station 40. For example, the fixed portion may be part of the frame of the analyzer. The arm 22 pivots around pin 23, which is perpendicular to the path of travel (P). The movable support is biased against the cuvette 50 that passes through the measurement station 40 by biasing means, such as leaf spring 24 anchored at one end 27 on the measurement station and at the other end 28 against the free end 25 of the movable arm. To prevent the biasing means from pushing the movable support excessively into the travel path of the cuvette when the cuvette is not present, a fixed stop 26 is provided to stop the lateral or inward motion of the movable arm into the path of travel P. The fixed support is mounted to the measurement station by pins 32 perpendicular to the path of travel P. The pins referred to above are meant to include any suitable fastening device, such as screws or bolts.

In the embodiment shown in the figures, the cuvette 50 includes a pickup hook 51 to engage the end of a conveying device that will translate the cuvette along the path of travel P during the measuring process. As shown in FIG. 3, the read window 52 is directly below the roller 21 (not shown in FIG. 3) and roller 31 as shown by the centerline 53 of the read window 52 passing directly through the center of the roller 31.

Figure 4:
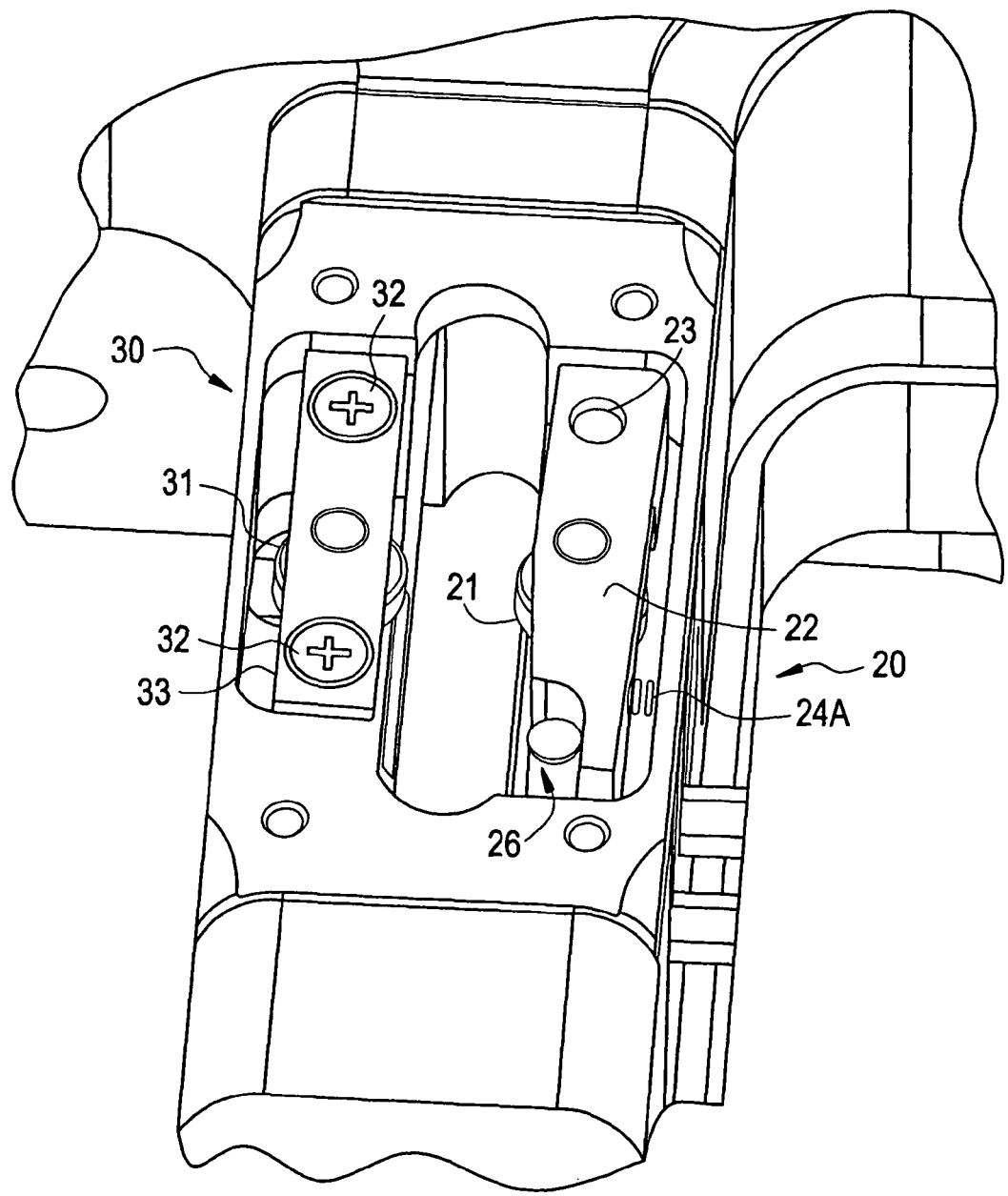
FIG. 4 is a top perspective view of the stabilizing device according to another embodiment of the present invention without a cuvette in a measuring station of an analyzer.
Figure 5:
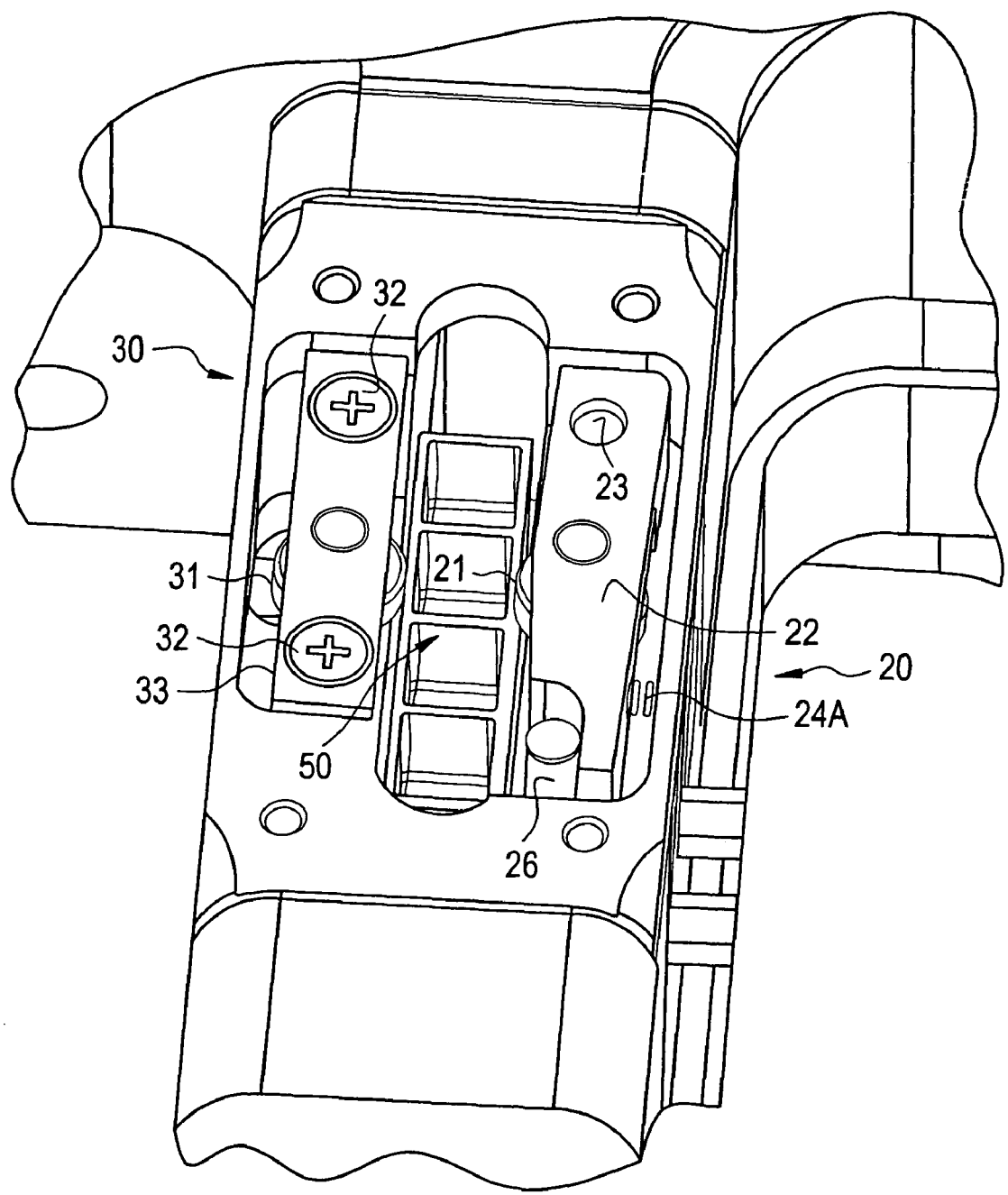
FIG. 5 is a top perspective view of the stabilizing device according to the embodiment in FIG. 4 with a cuvette in a measuring station of an analyzer.
Figure 6:
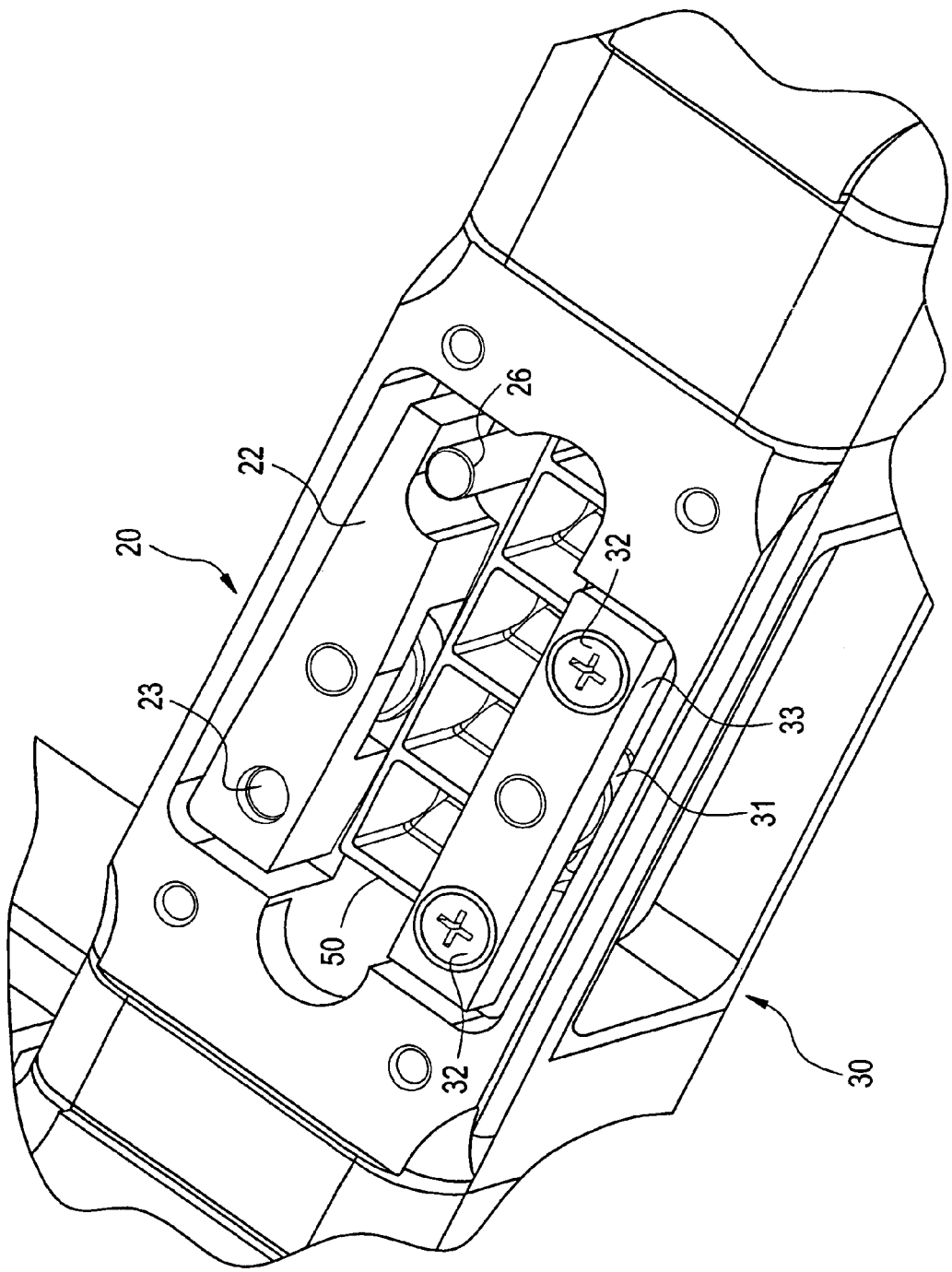
FIG. 6 is a top perspective view of the stabilizing device according to the embodiment in FIG. 4 with a cuvette in a measuring station of an analyzer.

FIGS. 4 to 6 show another embodiment of the present invention where a coil spring 24A is used to bias the movable arm into the path of travel P. Otherwise, the other elements correspond to those shown in FIGS. 2 and 3.

The present invention also provides a method for stabilizing the cuvette. This aspect entails using the device for stabilizing as described above. The cuvette, having a sample and optionally a reagent, is transported along the path of travel through the measurement station by a conveyor, such as the cuvette pickup arm described above. As the cuvette is transported through the measurement station it is engaged by the device for stabilizing where the movable support biases the cuvette against the fixed support. The cuvette is sandwiched between the movable and fixed support to reduce or more preferably eliminate lateral or side to side movement (shown as "L" in FIG. 2) of the cuvette at the optical measurement station. In a preferred embodiment, the device for stabilizing is in line with the measurement read window of the measurement device and the optically transparent window of the cuvette and its contents are being measured. That is, in the preferred embodiment, shown in the figures, the centerline of the roller 21 and 31 intersects the centerline of the measurement read window and cuvette which are in place. This helps to assist in minimal or no motion of the cuvette at the point the light is entering the cuvette.

The device of the present invention can also be used in connection with an analyzer for analyzing a sample, such as clinical or chemistry analyzer which are well known in the art and are described in such publications as U.S. patent Publication Nos. 2003/0022380 A1 and 2003/0104634 A1 and WO 2004/027375, which are incorporated herein by reference in their entireties. The analyzer includes a cuvette supply, such as a cuvette supply described in U.S. application Ser. No. 10/684,536 filed Oct. 14, 2003 and U.S. Pat. Nos. 6,328,164 and 4,636,477. Also included is one or more cuvettes, preferably multi-cell cuvettes such as those described above. A sample supply such as that described in the '380 publication is also included along with a metering station for metering sample and optionally reagent from the sample (reagent) supply into the cuvette. In some embodiments, the metering station for metering sample and reagent may be different. An incubator is optionally provided for incubating cuvettes prior to measurement in the measurement station. All these aspects of an analyzer are well known in the art and do not need to be described in detail.

An optical measurement station having a light source and detector as described above is also included. In a preferred embodiment, the optical measurement station is a spectrophotometer.

A cuvette conveyor is provided for conveying cuvettes from the cuvette supply past the metering station and to the optical measurement station. The cuvette conveyor can be any suitable device capable of transporting the cuvette into and out of the measurement station. In some instances, the conveyor may transport the cuvette into an entrance and out of another exit in the measurement station. Alternatively, the conveyor may transport the cuvette into and out of the same entrance/exit. In a preferred embodiment, the cuvette conveyor is a cuvette pickup arm that engages the cuvette at one end in a cantilevered fashion, such as by hook 51 and pushes/pulls the cuvette into and out of the measurement station. Other embodiments can include, e.g., a chain conveyor that engages the cuvette at the bottom and transports the cuvette through the measurement station.

In those embodiments, where the cuvette conveyor is a cuvette pickup arm, an improved ramping profile will also contribute to improving the stability of the cuvette by reducing the drive system vibration from being translated into cuvette motion during the read process. A conventional system uses a stepping motor taking a fixed amount of a full step at the motor of 1.8 degrees. This creates a relatively stiff system and uncontrolled accelerations for the small amount of motor movements required (2 full steps). This problem can be solved by using a smaller step angle of ¼ a 0.24 degree step angle or greater. At $\frac{1}{16}$ of a step angle the motor moves 0.1125 degrees and if the moves or steps are spread out over time the acceleration of the system is controlled, therefore reducing unwanted mechanical vibrations. The changes made to accomplish this were as follows:

| Preferred Motor Control | Conventional Motor Control |
| --- | --- |
| 16th Step | ¼ Step |
| 8 Acceleration Steps | 2 Acceleration Steps |
| 8 Deceleration Steps | 2 Deceleration Steps |
| Total Steps: | |
| 32 | 8 |
| Run Current: | |
| 0.72 amps | 0.86 amps |
| Hold Current: | |
| 0.43 amps | 0.28 amps |
| Slew Rate: | |
| 1600 $\frac{1}{16}$ Steps/Sec | 800 ¼ Steps/Sec |

The motor control improvements described above enable a 2 times or greater improvement in photometer absorbance measurement precision across the full absorbance range from 0 to 3 AU.

The motor control improvements are especially useful in those embodiment employing measurement reads at multiple locations within a single cell. As described above, the inventors found that the first measurement read in the cell was unexpectedly more precise than the remaining measurement reads within the same cell. This is believed to be due to the nature of the incremental cuvette advance between subsequent measurement reads, which results in a jerking motion. The motor control improvements described directly above have been found to reduce the vibration energy during the subsequent measurement reads such that the stabilization device did not have to remove as much energy.

The present invention can be used in a method for measuring the presence of concentration of an analyte in a sample by spectrophotometry. Broadly, the method involves transporting the sample contained in a cuvette into the measurement station using the device for stabilizing cuvette as described above. A light source directs a beam of light from a light through the sample to be measured at least one location on the cuvette, which has been stabilized as described above. The amount of light emitted from the cuvette and sample is then measured and the concentration of the analyte in the sample can then be measured using techniques well known in the art.

In a preferred embodiment two or more measurement reads are taken for each cuvette at different locations on the cuvette. The measurement reads are compared with one another. Based upon the comparison, in particular the difference in the measurement reads of emitted light of these samples, one can determine whether there has been: an error in one or more of the measurement reads and take appropriate action, such as discarding or disregarding one or more of the measurement reads as an outlier and using the remaining measurement reads for the analysis, or alternatively disregarding all measurement reads and either remeasuring the sample in the same cuvette or preparing a new sample for measurement read; or whether there are no significant errors such that all measurement reads are considered acceptable, in which case, all measurement reads can be used, or more preferably one of the measurement reads can be used, e.g., the highest or lowest, depending on the type of analysis being conducted. This method is described in copending application U.S. Ser. No. 10/784,505 previously described above. In a preferred embodiment, the integration time for the measurement read is 40 ms or less, more preferably 20 ms or less.

The measurement method according to the present invention can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:

1. An analyzer for analyzing a sample comprising:
   a cuvette supply;
   one or more cuvettes, wherein the cuvettes each comprise a cantilever;
   a sample supply;
   a metering station for metering sample from the sample supply into the cuvette;
   an optical measurement station having a light source and detector for taking an optical measurement read of the sample, wherein the path of the light source and detector forms a measurement window;

a cuvette conveyor for conveying cuvettes from the cuvette supply to the metering station and to the optical measurement station, wherein the cuvettes are mounted in the conveyor by cantilevering them; and a device for stabilizing a cuvette during a measurement read in the analyzer having a cuvette path of travel, comprising:

a fixed support located on a first side of the path of travel having a first roller being located on the fixed support and directly abutting a side of the cuvette at a location that does not interfere with an optical window on the cuvette on which the measurement read takes place; and a movable support located on a second side of the path of travel having a second roller directly abutting a side of the cuvette being located directly opposite the first roller on the movable support at the location that does not interfere with the measurement read and wherein the centerline of the measurement window passes through the centerline of the first and the second rollers, wherein said device is located in the optical measurement station, and wherein the light source is located on the first or second side of the path of travel and the detector is located the other side of the path of travel.

2. The analyzer as claimed in claim 1, wherein the analyzer is a chemistry analyzer.

3. The analyzer as claimed in claim 1, wherein the analyzer is a diagnostic analyzer.

4. The analyzer as claimed in claim 1, wherein the cuvette is a multicell cuvette.

5. The analyzer as claimed in claim 1, wherein the movable support comprises an elongated member having a distal and proximal end with the second roller being located between the distal end and proximal end and wherein the proximal end is pivotably anchored and the distal end is free.

6. The analyzer as claimed in claim 5, wherein the first and second roller contact the cuvette at a location above the optical window on the cuvette on which the measurement read takes place.

7. The analyzer as claimed in claim 5, further comprising a stop located at a position in the vicinity of the distal end of the movable support to prevent the movable arm from contacting or coming within a selected distance from the fixed support when the cuvette is not positioned between the fixed and movable support.

8. The analyzer as claimed in claim 5, further comprising a biasing device located at a position to bias the second roller in a direction toward the fixed support.

9. The analyzer as claimed in claim 8, wherein the biasing device is a leaf spring having one end attached to the measurement station and another end pressing against the elongated member.

10. The analyzer as claimed in claim 8, wherein the biasing device is a coil spring having one end attached to the measurement station and another end pressing against the elongated member.

11. The analyzer as claimed in claim 5, wherein the fixed support is supported by pins which are perpendicular to the path of travel of the cuvette.

12. The analyzer as claimed in claim 5, wherein the movable member is rotabably supported by a pin which is perpendicular to the path of travel of the cuvette.

13. The analyzer as claimed in claim 1, wherein the cuvette comprises multiple chambers arranged side-by-side wherein said chambers have at least one optically transparent window pair to measure an optical property.

14. The analyzer as claimed in claim 1, wherein the cuvette conveyor is a cuvette pickup arm that engages the cuvette at one end by cantilevering and pushes/pulls the cuvette into and out of the measurement station.

* * * * *